(12) United States Patent
Keane

(10) Patent No.: US 6,960,206 B2
(45) Date of Patent: Nov. 1, 2005

(54) COILED ABLATION CATHETER SYSTEM

(75) Inventor: David Keane, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 204 days.

(21) Appl. No.: 10/462,347

(22) Filed: Jun. 16, 2003

(65) Prior Publication Data
US 2003/0208199 A1 Nov. 6, 2003

Related U.S. Application Data

(63) Continuation of application No. 09/396,959, filed on Sep. 15, 1999, now Pat. No. 6,607,520.

(51) Int. Cl.[7] .............................................. A61B 18/18
(52) U.S. Cl. ........................................................ 606/41
(58) Field of Search ...................... 606/27–52; 607/101, 607/122

(56) References Cited

U.S. PATENT DOCUMENTS

| 5,060,660 A | * | 10/1991 | Gambale et al. ............. 128/772 |
| 5,156,151 A | | 10/1992 | Imran .......................... 128/642 |
| 5,239,999 A | | 8/1993 | Imran .......................... 128/642 |
| 5,279,299 A | | 1/1994 | Imran .......................... 128/642 |
| 5,281,218 A | | 1/1994 | Imran .......................... 606/41 |
| 5,403,311 A | | 4/1995 | Abele et al. ................... 606/49 |
| 5,404,638 A | | 4/1995 | Imran .......................... 29/884 |
| 5,406,946 A | | 4/1995 | Imran .......................... 128/642 |
| 5,431,168 A | | 7/1995 | Webster, Jr. ................. 128/658 |
| 5,476,495 A | | 12/1995 | Kordis et al. ................ 607/122 |
| 5,484,384 A | | 1/1996 | Fearnot ......................... 600/3 |
| 5,507,743 A | | 4/1996 | Edwards et al. .............. 606/41 |
| 5,517,989 A | * | 5/1996 | Frisbie et al. ................ 128/642 |
| 5,573,531 A | | 11/1996 | Gregory ....................... 606/14 |
| 5,582,609 A | | 12/1996 | Swanson et al. |
| 5,593,405 A | | 1/1997 | Osypka ........................ 606/15 |
| 5,617,854 A | | 4/1997 | Munsif ........................ 128/642 |
| 5,680,860 A | * | 10/1997 | Imran .......................... 600/374 |
| 5,738,683 A | | 4/1998 | Osypka ........................ 606/47 |
| 5,782,899 A | | 7/1998 | Imran .......................... 607/122 |
| 5,807,306 A | | 9/1998 | Shapland et al. ............. 604/21 |
| 5,807,395 A | | 9/1998 | Mulier et al. ................. 606/41 |
| 5,836,940 A | | 11/1998 | Gregory ....................... 606/15 |
| 5,836,947 A | * | 11/1998 | Fleischman et al. .......... 606/47 |
| 5,895,398 A | | 4/1999 | Wensel et al. ............... 606/159 |
| 5,980,563 A | * | 11/1999 | Tu et al. ...................... 607/113 |
| 6,012,457 A | | 1/2000 | Lesh .......................... 128/898 |
| 6,024,740 A | | 2/2000 | Lesh et al. ................... 606/34 |
| 6,102,908 A | * | 8/2000 | Tu et al. ...................... 606/41 |
| 6,228,109 B1 | * | 5/2001 | Tu et al. ...................... 607/113 |
| 6,245,067 B1 | * | 6/2001 | Tu et al. ...................... 606/41 |
| 6,280,441 B1 | * | 8/2001 | Ryan ........................... 606/45 |
| 6,322,559 B1 | * | 11/2001 | Daulton et al. ............... 606/41 |
| 6,325,797 B1 | | 12/2001 | Stewart et al. |

FOREIGN PATENT DOCUMENTS

| EP | 0 626 153 | 11/1994 | |
| WO | WO 0042934 | 7/2000 | ........... A61B/18/14 |

* cited by examiner

Primary Examiner—Michael Peffley
Assistant Examiner—Pete Vrettakos
(74) Attorney, Agent, or Firm—Nutter, McClennen & Fish LLP

(57) ABSTRACT

A cardiac ablation catheter includes a coil-like ablating element that is deployable from an elongate, flexible sheath. The ablating element, while in the deployed position, has a shape with at least one revolution oriented in a plane that is orthogonal to a longitudinal axis of the sheath. The catheter system is well-suited to ablate a circumferential region of tissue about a pulmonary vein or the posterior wall of the left atrium proximate the pulmonary vein os. The treated tissue region electrically isolates the atria from the pulmonary vein.

17 Claims, 4 Drawing Sheets

COILED ABLATION CATHETER SYSTEM

CROSS-REFERENCE TO RELATED APPLICATIONS

This application is a continuation of application Ser. No. 09/396,959 filed Sep. 15, 1999, now U.S. Pat. No. 6,607,520 titled "Coiled Ablation Catheter System," which is hereby incorporated by reference in its entirety.

STATEMENT REGARDING FEDERALLY SPONSORED RESEARCH

Not Applicable.

FIELD OF THE INVENTION

The present invention relates generally to catheter systems, and more particularly, to catheter systems for ablating and/or isolating foci that contribute to cardiac arrhythmia.

BACKGROUND OF THE INVENTION

Catheters are commonly used in surgical procedures to access certain areas of a patient=s body without resorting to invasive surgical procedures. For example, catheters are widely used in the field of cardiology to conduct electrophysiological studies in which electrical potentials within the heart are mapped to determine the cause and location of arrhythmia. In many cases, certain undesired conductive pathways, known as foci, contribute to and cause the arrhythmia. Once the location of foci is identified, elements on or within the catheter can be utilized to ablate or isolate the foci, thus eliminating the arrhythmia.

One form of arrhythmia is atrial fibrillation, which is an uncoordinated contraction of the heart muscle within the atrium. Atrial fibrillation results from rapidly discharging foci and causes irregular heart beats, possibly leading to inefficient pumping of blood. In a significant number of patients, the foci that contribute to this condition are located within the pulmonary vein, adjacent to the atrium. These foci may be in the form of scattered groups of rapidly discharging cells. Treatment of this condition can sometimes be effective through the ablation of these foci. However, identifying the location of these foci and effecting the ablative treatment of the foci can be time consuming and difficult.

A variety of cardiac mapping and ablation catheter systems are well known in the art. For example, U.S. Pat. No. 5,476,495 (Kordis et al.) discloses a steerable catheter system that is able to conduct cardiac mapping and ablation. U.S. Pat. No. 5,507,743 (Edwards et al.) discloses a radio frequency (RF) treatment apparatus that includes a RF electrode that assumes a helical orientation upon deployment. U.S. Pat. No. 5,738,683 (Osypka) discloses a cardiac mapping/ablation catheter that includes an electrode that may be deployed in the shape of a loop. U.S. Pat. No. 5,782,879 (Imran) discloses an endocardial mapping and ablation system in which the catheter includes a deployable distal extremity, in the form of a cage-like member that includes a plurality of electrodes.

Despite the existence of these references and existing ablation catheter systems, there exists a need to provide a system that is able to effectively treat atrial fibrillation conditions that are caused by foci present within the pulmonary vein.

SUMMARY OF THE INVENTION

The present invention provides a cardiac catheter system for ablating tissue to electrically isolate certain tissue from arrhythmia-inducing foci. Although the invention is primarily shown and described as a cardiac catheter system for ablating tissue with RF energy, it is understood that the system has other applications and embodiments as well. For example, other types of energy, such as microwave, laser, cryogenic, and ultrasonic energy, can be used without departing from the scope of the invention.

In one embodiment, a cardiac ablation catheter system includes an elongate, flexible sheath having an internal lumen and an open distal end. An ablating element is disposed within the sheath and is selectively deployable therefrom so as to project from the sheath in a substantially coil-like shape. In an exemplary embodiment, the deployed ablating element has a geometry forming at least one revolution for generating a circumferential lesion within a vessel, such as a pulmonary vein. In general, the ablating element is oriented in a plane that is substantially orthogonal to the longitudinal axis of the sheath in the deployed position to facilitate the formation of a lesion about the vein inner wall circumference.

The catheter system can include a variety of mechanisms for deploying the ablation member from the catheter. In one embodiment, the ablation member is released from a distal end of the catheter such that it assumes a predetermined shape. In another embodiment, the catheter includes a hatch or port from which the ablation member is selectively deployed. In a further embodiment, the elongate member includes a distal end affixed to a support member that is extendable from the catheter distal end. By rotating and/or longitudinally displacing the support member, the ablation member can be deployed such it assumes a desired size.

To ablate or isolate the target foci tissue, the catheter is manipulated through the arterial network until the catheter is located proximate the desired treatment site. For example, the treatment site may be a location within the pulmonary vein or left atrium at or near the pulmonary vein os or in the right ventricular outflow tract, such as at the junction of the right atrium and superior vena cava. The ablating element is then deployed from the catheter such that the coil-like ablating element is generally oriented in a plane orthogonal to the longitudinal axis of the sheath. The deployed ablating element should be in contact with tissue about the circumference of the vein inner wall, such as at the os. The ablation element is then energized to ablate the target tissue to electrically isolate the foci from healthy tissue on the opposite side of the formed lesion. The atria, for example, can be electrically isolated from a treated pulmonary vein by creating a circumferential lesion on the inner wall of the left atrium or in the pulmonary vein proximate the os.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
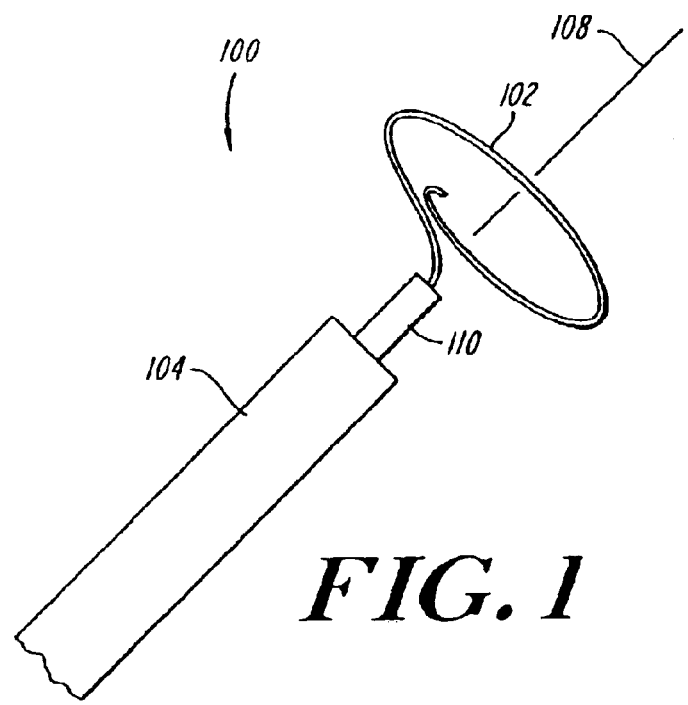
FIG. 1 is a perspective view of an ablation catheter system in accordance with the present invention.
Figure 2:
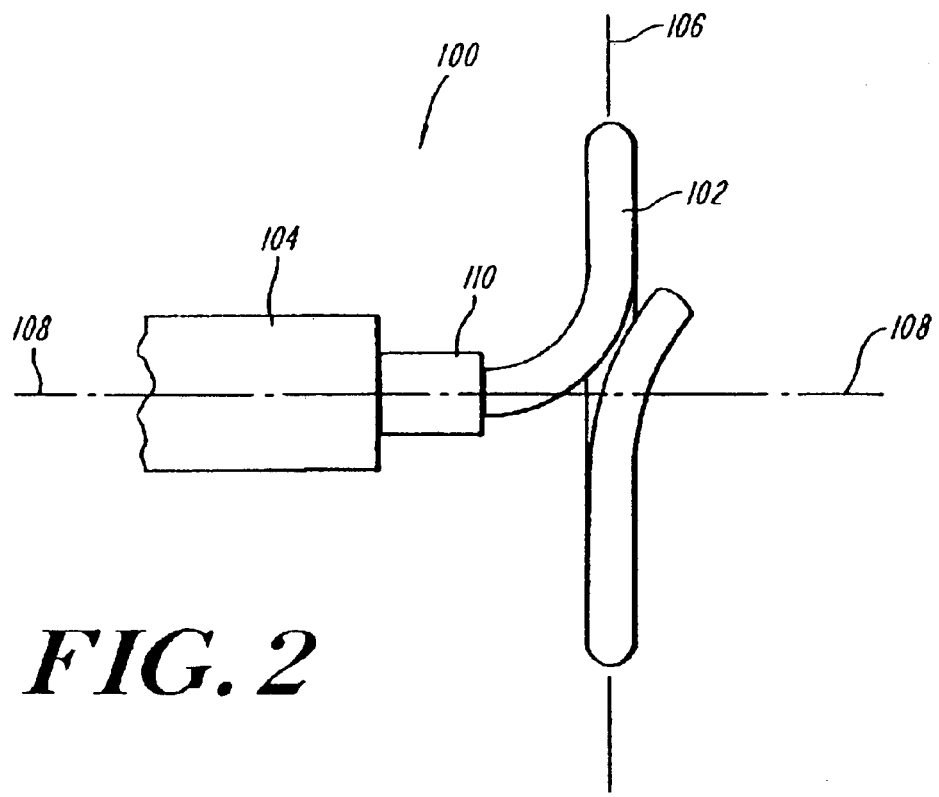
FIG. 2 is a side view of a portion of the catheter system of FIG. 1.
Figure 3:
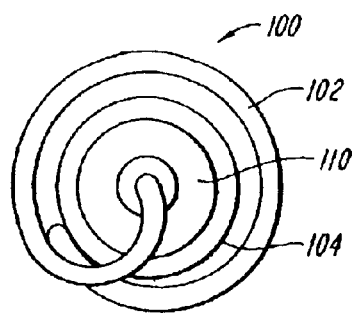
FIG. 3 is a front view of a portion of the catheter system of FIG. 1.
Figure 4:
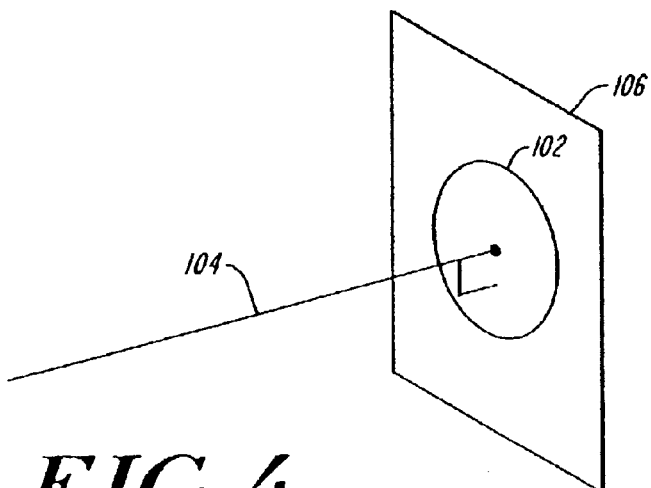
FIG. 4 is a pictorial representation of the orientation of an ablating element in a deployed position and a catheter that forms a part of the catheter system of FIG. 1.

FIGS. 1–3 show an ablation catheter system 100 in accordance with the present invention having an ablation element 102 that is deployable from a flexible elongate catheter or sheath 104. The catheter sheath 104 should be semi-rigid and flexible so as to be readily steerable to a desired location in a patient=s body, such as proximate the os of a pulmonary vein. Such catheter delivery systems are well known to those of ordinary skill in the art. In general, the deployed coil-like ablation element 102 has a shape that includes one or more revolutions substantially oriented in a transverse plane 106 (FIG. 4) that is orthogonal to a longitudinal axis 108 of the sheath 104. This geometry facilitates treating tissue about a circumference of a vessel, such as a pulmonary vein. The circumferential region of ablated tissue electrically isolates tissue on opposite sides of the ablated tissue. Thus, the atria, for example, can be electrically isolated from any arrhythmia-inducing foci within the pulmonary vein.

In one embodiment, the catheter system 100 includes a tubular inner member 110 for housing the ablation member 102 in the non-deployed position. In general, it is preferred that the inner member 102 be formed from an insulative material to prevent unintended contact with tissue, for example. Exemplary materials for the insulative inner member 110 include Teflon and polyethylene.

The elongate ablation element 102 can have a variety of geometries that are effective to form a generally annular lesion about a circumference of a vessel wall. Exemplary geometries include annular shapes having one or more revolutions, crenulated, corrugated, and combinations thereof. It is understood that the term Arevolution@ should be construed broadly to include configurations of somewhat less than three hundred and sixty degrees. It is further understood that the transverse plane 106 on which the revolutions of the elongate member are located provides a general frame of reference and that the elongate member can vary in distance from the plane as the elongate member forms a revolution. In the exemplary embodiment of FIGS. 1–3, which shows the ablation member 102 in the deployed state, the ablation member 102 has a coil-like appearance that forms approximately one revolution generally oriented in the transverse plane 106 that is substantially orthogonal to a longitudinal axis 108 of the sheath. This configuration is well-suited for contacting a vessel inner wall about its circumference or for contacting the posterior wall of the left atrium to circumscribe the os of a pulmonary vein. The resultant circumferential lesion on the atrial or vessel wall can be effective to isolate electrical impulses from the offending foci from passing to healthy tissue on the opposite side of the lesion.

Figure 5:
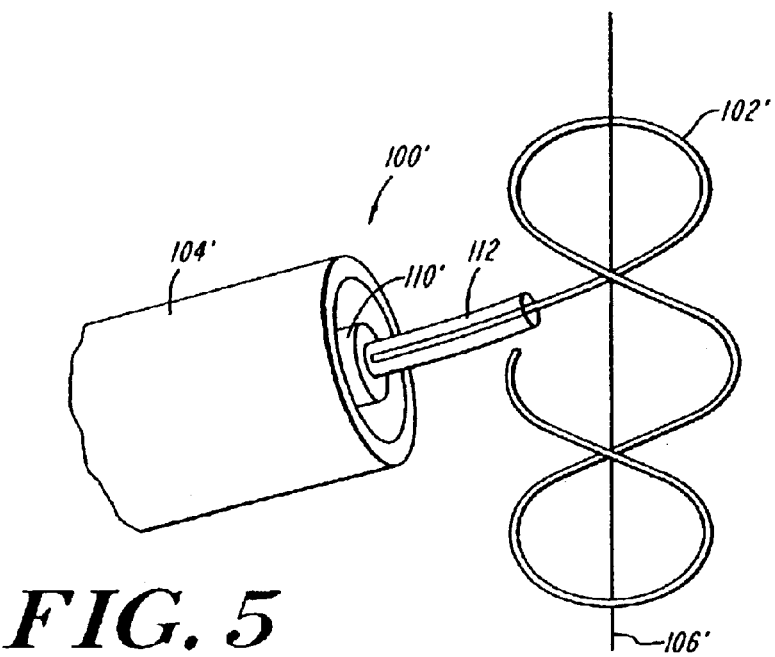
FIG. 5 is a perspective view of an alternative geometry for an ablating element.

FIG. 5 shows the catheter system 100' including an ablation member 102' having an alternative, crenulated geometry. That is, the ablation member 102' undulates so as to intersect the transverse plane 106' at defined intervals along a revolution. This configuration may inhibit or limit stenosis of the treated vessel proximate the circumferential lesion. The ablation member 102' can be partly surrounded by an insulative coating 112.

In one embodiment, the ablation member 102 is formed from a conductive elastic or superelastic shape memory material for ablating tissue with RF energy. Exemplary shape memory materials include nickel-titanium alloys, such as Nitinol, and copper based alloys.

It is understood that shape memory materials, in general, can be plastically deformed from a first shape at a relatively low temperature. Upon heating the material to some higher temperature, such as by resistive heating, the material will tend to return to the first shape. Such materials can have so-called one-way and two-way shape memories.

In further embodiments (not shown), the ablation member can be at least partly surrounded by an insulative coating. The insulative coating can be disposed on the ablation member so as to form a plurality of discrete electrodes for ablating tissue at selected locations along the vessel circumference.

The ablation element can be deployed from the sheath using a variety of mechanisms that are compatible with steerable catheter systems. Exemplary mechanisms include predetermined shapes for the elongate member, manual deployment mechanisms, and guidewire based mechanisms.

Figure 6:
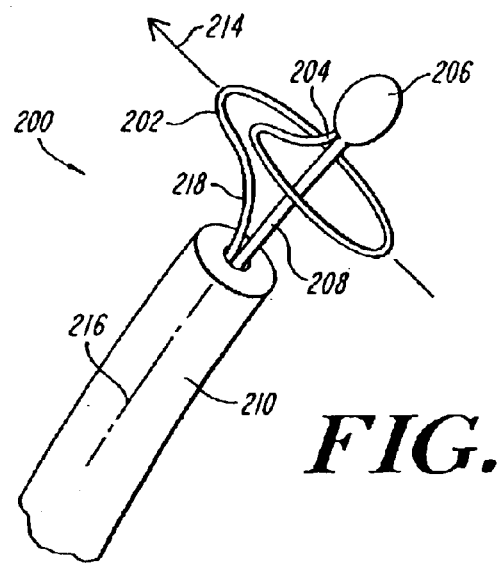
FIG. 6 is a perspective view of a further embodiment of an ablation catheter system in accordance with the present invention.

FIG. 6 shows an ablation catheter system 200 having an ablation member 202 with a distal end 204 secured to a bulbous end 206 of a support member 208. The support member 208 is disposed within the sheath 210 and connected to an actuator (not shown) at a proximal end of the catheter. To deploy the ablation member 202, the support member 208 is longitudinally displaced with respect to the sheath such that the bulbous end 206 protrudes from the end 212 of the catheter. Upon exiting the sheath 210, the ablation member 202 assumes a predetermined shape that includes about one revolution in a transverse plane 214 orthogonal to the sheath longitudinal axis 216. The ablation member 202 can extend from a retractable support wire 218.

In one embodiment, the bulbous end 206 of the support member is radiopaque to facilitate determining the ablation member position on an external viewing system, such as an X-ray system.

Alternatively, the ablation member 202 can be wound on the support member 208 in the non-deployed state. The support member 208 can be rotated in a predetermined direction such that the ablation member 202 is unwound or released from the support member. The support member 208 can be rotated until the ablation member extends from the support member a desired distance. After ablation, the ablation member 202 can be retracted to the non-deployed state by rotating the support member in the opposite direction.

Figure 7:
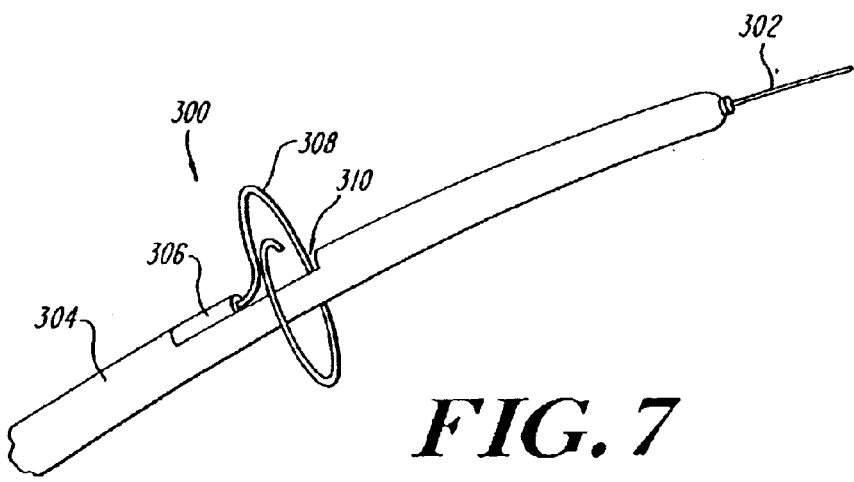
FIG. 7 is a perspective view of another embodiment of an ablation catheter in accordance with the present invention.

FIG. 7 shows an ablation catheter system 300 including a guide wire 302 for manipulating a catheter 304 within the patient=s body. It is understood that the guide wire 302 can be utilized in conjunction with mapping systems (which may be separate from or integral with the catheter system 300) to locate arrhythmic foci. The catheter 304 includes a hatch 306 from which an ablation member 308 can be deployed. Upon actuating the hatch 306 to the open position, the ablation member 308 discharges from the resultant opening 310 and assumes a predetermined configuration. It is understood that the predetermined annular shape will be effective to contact vessel walls having a circumference less than or equal to a predetermined value, which by way of example, may be in the range of about 0.4 centimeters to about 4.0 centimeters.

Figure 7A:
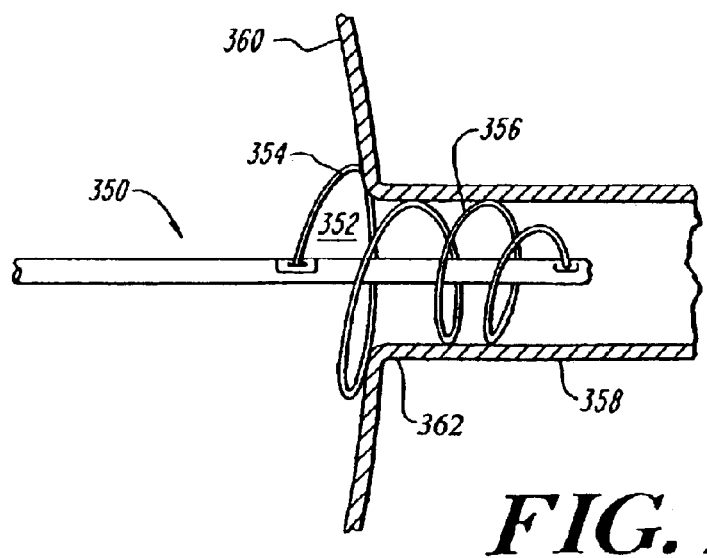
FIG. 7A is a pictorial representation of an alternative embodiment of an ablation catheter in accordance with the present invention.

FIG. 7A shows an alternative embodiment of a catheter system 350 including an ablation member 352 having an exposed proximal portion 354 for ablating tissue and an insulated distal portion 356 for centering the catheter within a pulmonary vein 358. The catheter system 350 is well suited for creating a circumferential lesion on the posterior left atrial wall 360 around the pulmonary vein os 362.

Figure 8A:
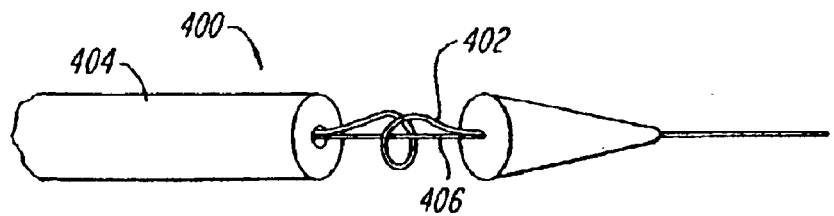
FIG. 8A is a pictorial representation of a further embodiment of an ablation catheter in accordance with the present invention shown in a first position.
Figure 8B:
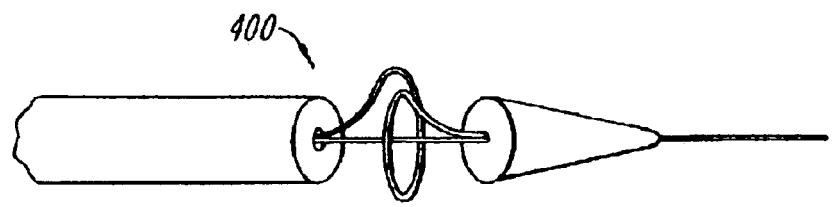
FIG. 8B is a pictorial representation of the catheter of FIG. 8A shown in a second position.
Figure 8C:
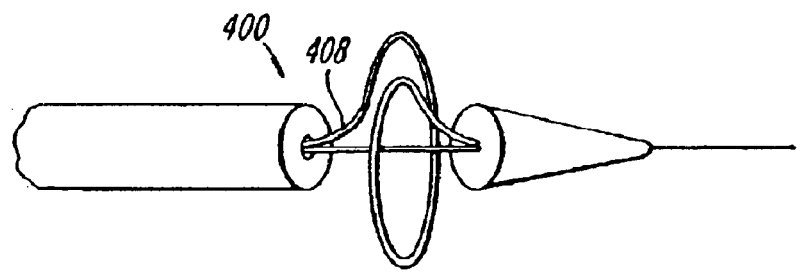
FIG. 8C is a pictorial representation of the catheter system of FIG. 8A shown in a a third position.

FIGS. 8A–C show a manually expandable ablation member 402 that forms a part of a cardiac ablation catheter system 400 in accordance with the present invention. The system 400 includes a guide-wire based catheter 404 with an ablation member 406 that is manually deployable from the catheter. In one embodiment, the ablation member 406 is coupled to a semi-rigid support member 408 (FIG. 8C) that can be rotated and/or longitudinally displaced so as to deploy the ablation member 402 $6$. The size of the loop formed by the ablation member 406 can be selected by controlling the amount of rotation/displacement of the support member 408. Alternatively, the leading end of the ablation element can be affixed to the guide wire. In one embodiment, the ablating element can be manipulated by rotating the guide wire.

Figure 9:
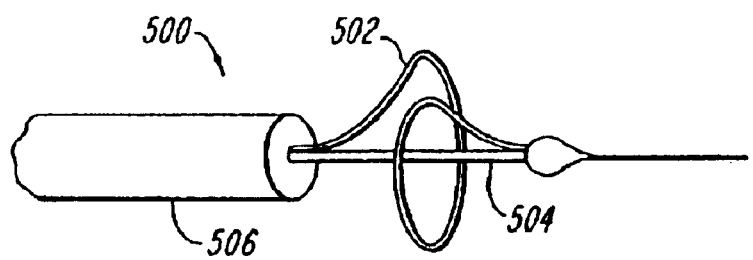
FIG. 9 is a perspective view of another embodiment of an ablation catheter system in accordance with the present invention.

FIG. 9 shows a further embodiment of a guide-wire based ablation catheter system 500 having a manually deployable ablation member 502. This system is similar to the system 200 shown in FIG. 6 with the addition of a guide wire 504 that can provide additional stability during ablation. The catheter 506 is mounted on the guide wire 504 to facilitate advancement of the catheter into the pulmonary vein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A cardiac catheter system, comprising:
   an elongate, flexible sheath having an internal lumen, a distal end and a longitudinal axis; and
   an ablating element disposed within the sheath and selectively deployable therefrom so as to project from the sheath to a pulmonary vein of a subject with a substantially coil-like shape having at least one revolution, wherein the ablating element, in a deployed condition, is oriented in a plane that is substantially orthogonal to the longitudinal axis of the sheath;
   the ablating element having a tissue contacting portion that is continuously conductive, the continuously conductive region being positioned on the ablating element such that when so deployed it ablates a circumferential blocking lesion in the region of said pulmonary vein; and
   a guide wire disposed within and selectively deployable from the sheath, wherein a leading end of the ablating element is secured to the guide wire.

2. The system of claim 1, wherein the ablating element is self-expanding and assumes a predetermined shape upon deployment from the sheath.

3. The system of claim 2, wherein the ablating element is made from a shape-memory material.

4. The system of claim 3 wherein the shape-memory material is selected from the group consisting of nickel-titanium alloys and copper-based alloys.

5. The system of claim 3 wherein the shape-memory material is superelastic.

6. The system of claim 3, wherein the shape-memory material has a two-way shape memory.

7. The system of claim 1 wherein the ablating element further comprises a terminal which is connectable to an energy source selected from the group consisting of radio frequency energy, laser energy, microwave energy, ultrasonic energy, and cryogenic energy.

8. The system of claim 1, wherein the ablating element is manually and selectively expandable from the sheath.

9. The system of claim 1 wherein the coil-like shape has a radius which expands as the ablating element advances from the sheath.

10. The system of claim 1 wherein the guide wire extends along a longitudinal axis of the sheath, and the ablating element is expandable from the sheath by rotating the guide wire about the longitudinal axis of the sheath.

11. The system of claim 1, wherein the leading end of the ablating element is surrounded by an insulating material.

12. The system of claim 1, wherein a lagging end of the ablating element is uninsulated and forms the coil-like shape of the ablating element.

13. The system of claim 1, further comprising a non-conductive, insulating element disposed within the sheath and selectively deployable therefrom, wherein the ablating element is deployable from within the non-conducting, insulating element.

14. The system of claim 13 wherein the ablating element is retractable into the non-conductive, insulating element.

15. The system of claim 1, wherein the at least one exposed, conductive region further comprises a plurality of discrete electrodes.

16. The system of claim 1, wherein the coil-like shape of the ablating member has a crenulated circumferential region.

17. A cardiac catheter system, comprising
   an elongate, flexible sheath having dimensions suitable for intravascular passage and a longitudinal axis;
   a guide wire disposed within the sheath and selectively deployable from a distal end of the sheath;
   an ablating element disposed within and selectively deployable from the distal end of the sheath in concert with the guide wire, the ablating element having a leading end secured to the guide wire and a trailing portion disposed within the sheath; and an ablating element deployment mechanism that is effective to advance at least a portion of the trailing portion of the ablating element out of the distal end of the sheath by a predetermined distance to cause the ablating element to assume a coil-like shape, with a tissue contacting portion that is continuously conductive and effective to ablate a circumferential blocking lesion in the region of a pulmonary vein.

* * * * *